US010296714B2

(12) United States Patent
Goldstein et al.

(10) Patent No.: US 10,296,714 B2
(45) Date of Patent: May 21, 2019

(54) METHOD AND SYSTEM FOR MEDICAL CANNABINOID TREATMENT AND PRODUCT SELECTION

(71) Applicant: Potbotics, Inc., New York, NY (US)

(72) Inventors: Boris Goldstein, New York, NY (US); David Goldstein, New York, NY (US); Milla Bakhareva, New York, NY (US)

(73) Assignee: Potbotics, Inc., New York, NY (US)

( * ) Notice: Subject to any disclaimer, the term of this patent is extended or adjusted under 35 U.S.C. 154(b) by 541 days.

(21) Appl. No.: 15/153,404

(22) Filed: May 12, 2016

(65) Prior Publication Data

US 2016/0335543 A1    Nov. 17, 2016

Related U.S. Application Data

(60) Provisional application No. 62/161,254, filed on May 13, 2015.

(51) Int. Cl.
*G06N 5/02* (2006.01)
*G06F 19/00* (2018.01)
*G06F 17/27* (2006.01)
*G06F 17/28* (2006.01)

(52) U.S. Cl.
CPC ........ *G06F 19/324* (2013.01); *G06F 17/2785* (2013.01); *G06F 17/2881* (2013.01); *G06N 5/022* (2013.01)

(58) Field of Classification Search
CPC ... G06N 5/02; G06F 17/2785; G06F 17/2881; G06F 19/324
See application file for complete search history.

(56) References Cited

U.S. PATENT DOCUMENTS

| | | | |
|---|---|---|---|
| 2006/0167747 A1* | 7/2006 | Goodman | G06Q 30/02 705/14.53 |
| 2013/0297348 A1* | 11/2013 | Cardoza | G16H 10/60 705/3 |
| 2014/0214451 A1* | 7/2014 | Fung | G06F 19/324 705/3 |
| 2015/0112979 A1* | 4/2015 | Vittorio | G06F 17/30867 707/726 |

* cited by examiner

*Primary Examiner* — Austin Hicks
(74) *Attorney, Agent, or Firm* — Khanh T. Glatzel; Premium IP Services, P.C.

(57) ABSTRACT

This invention provides a computer method and system for interactive administration of medical cannabinoid treatments. The invention also provides information on cannabinoid product availability and geographical information. Medical professionals, cannabis growers, cannabis manufacturers, and other stakeholders can use this computer method and system to study trends, efficacy, and other information pertinent to the medical cannabis market.

16 Claims, 3 Drawing Sheets

METHOD AND SYSTEM FOR MEDICAL CANNABINOID TREATMENT AND PRODUCT SELECTION

CROSS REFERENCE TO RELATED APPLICATIONS

This claims the benefit of U.S. Provisional Application No. 62/161,254, filed May 13, 2015, which is incorporated by reference in its entirety.

BACKGROUND OF THE INVENTION

Field of the Invention

The present invention generally relates to a method operable in a computer readable medium and system for use by medical cannabis consumers, health professionals, growers, manufacturers, and sellers, which encompasses various computer interfaces, databases, and connectivity. This method and system utilize existing knowledge in the medical cannabis field while incorporating a newly built medical cannabis database for effective application of medical cannabis knowledge. Information collected from consumers is stored and aggregated for research purposes and may be used by medical professionals, growers, manufacturers, and other medical cannabis stakeholders to further develop the effectiveness of medical cannabis treatments and medical cannabis product provision.

Description of the Related Technology

The cannabis plant has many naturally occurring substances that are of great interest to scientific and medical communities. Isolated compounds from the cannabis plant include $\Delta^9$-tetrahydrocannabinol (THC), cannabidiol (CBD), cannabichromene (CBC), cannabigerol (CBG), cannabidivarin (CBDV), among other compounds. While THC has psychoactive effects, CBD, CBC, CBG, and CBDV do not. Isolated compounds from the cannabis plant are called "cannabinoids." There are a total of eighty-five (85) cannabinoids that have been isolated from the cannabis plant. Many researchers have confirmed the medicinal value of cannabinoids, including for the possible treatment of seizures, nausea, vomiting, lack of appetite, pain, arthritis, inflammation, and other conditions.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. These are among the most prominent compounds in the family of compounds extracted from the cannabis plant referred to as cannabinoids.

Cannabinoids may be isolated by extraction or cold pressing of cannabis plants. Plants in the cannabis genus include *Cannabis sativa, Cannabis ruderalis*, and *Cannabis indica*. These plants are the natural sources of cannabinoids. Cannabinoids are also available in synthetic forms. Methods to synthesize cannabinoids in lab settings were discovered and are currently practiced. Synthetic cannabinoids are more targeted than natural cannabinoids, in that the synthetic compound can come isolated without any other cannabinoids mixed in.

Cannabidiol is derived from hemp and is marketed in the United States as a dietary supplement. Various products containing cannabidiol have been marketed in recent years. Cannabidiol may be consumed by ingestion, by inhalation, or by transdermal delivery.

The cannabinoids CBD, CBG, and THC, have antibacterial properties, with fast acting mechanisms and a minimum inhibitory concentration at between 0.5-2 µg/ml for various *Staphylococcus aureus* strains.

Various medical marijuana products have become increasingly popular in the United States. Due to the placement of marijuana in Drug Enforcement Agency's Schedule I, the sale and prescription of medical marijuana has been limited in states where such practices are allowed. Recently, hemp products with cannabidiol became increasingly popular as an alternative. However, there is a clear gap in knowledge sharing in medical practices relating to medical marijuana.

Artificial intelligence is well utilized in medical practices, especially in integrating knowledge and assisting in dispensing rule-based decisions. Because medical knowledge is extensive, artificial intelligence plays a major role in updating and storing medical definitions and medical inter-relationships between many disparate concepts.

The Unified Medical Language System® (UMLS®) Metathesaurus® is a large, multi-purpose, and multi-lingual thesaurus that contains millions of biomedical and health related concepts, their synonymous names, and their relationships. The Metathesaurus® links alternative names and views of the same concept from different source vocabularies, and identifies useful relationships between different concepts.

The UMLS® also uses a Semantic Network, which contains a set of broad subject categories or semantic types that provide consistent categorization of all concepts represented in the UMLS® Metathesaurus® and a set of useful and important relationships, or semantic relations that exist between semantic types.

The third component of the UMLS® is the Specialist Lexicon. The Specialist Lexicon consists of a set of lexicon entries with one entry for each spelling, or set of spelling variants, in a particular part of speech. The Specialist Lexicon provides lexical information needed for the Specialist Natural Language Processing System.

Various medical software products exist to collect data on symptoms and diagnose patients. However, data collection and tracking patients' outcomes have not been focal points in these software products. In the medical cannabis field, due to Federal prohibition, there has been little development in merging medical cannabis use with information technology.

There exists a demand for a streamlined process to suggest and prescribe medical marijuana and related products through a database enabled by computer method with user interfaces. Data collected from the interactive process may be stored and used by medical professionals, producers, and marketers to evaluate trends and demands in the medical marijuana market.

SUMMARY OF THE INVENTION

This invention generally relates to databases, computer methods, and systems to carry out the computer methods, wherein the databases store information relating to various medical marijuana and cannabinoid products, various medical conditions treatable by medical marijuana and cannabinoid. The systems provide interactive means for various users to receive treatment, locate and supply products relating medical marijuana and cannabinoid therapy. The systems also analyze information collected from user interface modules to supply pattern to medical professionals and other stakeholders in the medical marijuana market.

According to embodiments, this invention relates to a method to provide medical cannabis diagnosis, treatment, information, and data analysis, including:

- displaying questions in natural language and receiving at least one answer from a user at a user interface;
- converting the at least one answer to computer readable data by a processor;
- processing the computer readable data by artificial intelligence reasoning using data from at least one knowledge source containing medical cannabis knowledge to produce at least one output;
- converting the at least one output into natural language; and
- displaying the at least one output in natural language at a user interface.

In some embodiments, in this method, the at least one answer is in natural language and the processor is a natural language processor. The knowledge source includes data from the Metathesaurus, the Semantic Network, and the Medical Marijuana Ontology; and the Medical Marijuana Ontology database includes medical marijuana data provided in computer readable files.

In some embodiments, the user interface in this method is a computing article, which may be a desktop computer, a laptop computer, a smart phone, a tablet, or a kiosk computer. The displayed questions in this method are adapted to the user type, which may be medical cannabis users, medical professionals, cannabis growers, cannabis producers, cannabis manufacturers, and cannabis salespersons.

In some embodiments, this method further includes the step of storing information received from the user, the step of uploading information to the knowledge source, and the step of receiving data from external sources to process received computer readable data.

According to embodiments, this invention also relates to a system for medical cannabis diagnosis, treatment, information provision, and data analysis, the system including:

- at least one user interface module;
- a first software architect to serve as the basis for the user interface module;
- a second software architect to serve as the single point data analysis;
- a third software architect to serve as the knowledge source; and
- at least one natural language processor to process user input into computer readable data;
- wherein the natural language processor processes or receives information from the at least one user interface module;
- wherein the second software architect receives information from the natural language processor and the third software architect; and
- wherein the third software architect processes information received from the second software architect and at least one outside source.

In the system as above, the at least one outside source includes the Metathesaurus, the Semantic Network, and the Medical Marijuana Ontology; while the at least outside source includes a Dynamic Unified Resource Identifier.

The Dynamic Unified Resource Identifier in this system includes:

- at least one existing knowledge database;
- at least one of an SQL server or a NoSQL server to receive and store data from the at least one existing knowledge database;
- at least one business intelligence tool;
- at least one medical cannabis business intelligence database; and
- a unified resource identifier;
- wherein the SQL and NoSQL servers supply data to the business intelligence tool;
- wherein the business intelligence tool supplies data to the medical cannabis business intelligence database; and
- wherein the medical cannabis business intelligence database and business intelligence tool analyze and supply data to the unified resource identifier.

In some embodiments, the system further includes at least one reusable module, and the at least one reusable module is a Point-of-Sale module, a Reservation module, or a History module. The system further includes at least one additional database to supply data to the third software architect, which may be a User Data database, a Reporting database, or an Analytics database. The system further includes at least one of an external service or an artificial programming interface.

ABBREVIATIONS

AI: Artificial Intelligence
API: Application Programming Interface
BI: Business Intelligence
DB: Database
MJ: Marijuana
MMJ: Medical Marijuana
NLP: Natural Language Processor
POS: Point-of-Sale
Q&A: Questions and Answers
REST: Representational State Transfer
UI: User Interface
URI: Uniform Resource Identifier

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean that items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoid" used in this specification, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol,(−)-(3S,4S)-7-hydroxy-delta-6-tetrahydrocannabinol-1,1-dimethylheptyl, (+)-(3S,4S)-7-hydroxy-$\Delta$-6-tetrahydrocannabinol, and $\Delta^8$-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendiol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

As used herein, the phrases "medical marijuana" and "medical cannabis" are used interchangeably, and are used to describe the use of products having *Cannabis sativa* L. plant components and/or cannabinoids to treat medical conditions.

Figure 1:
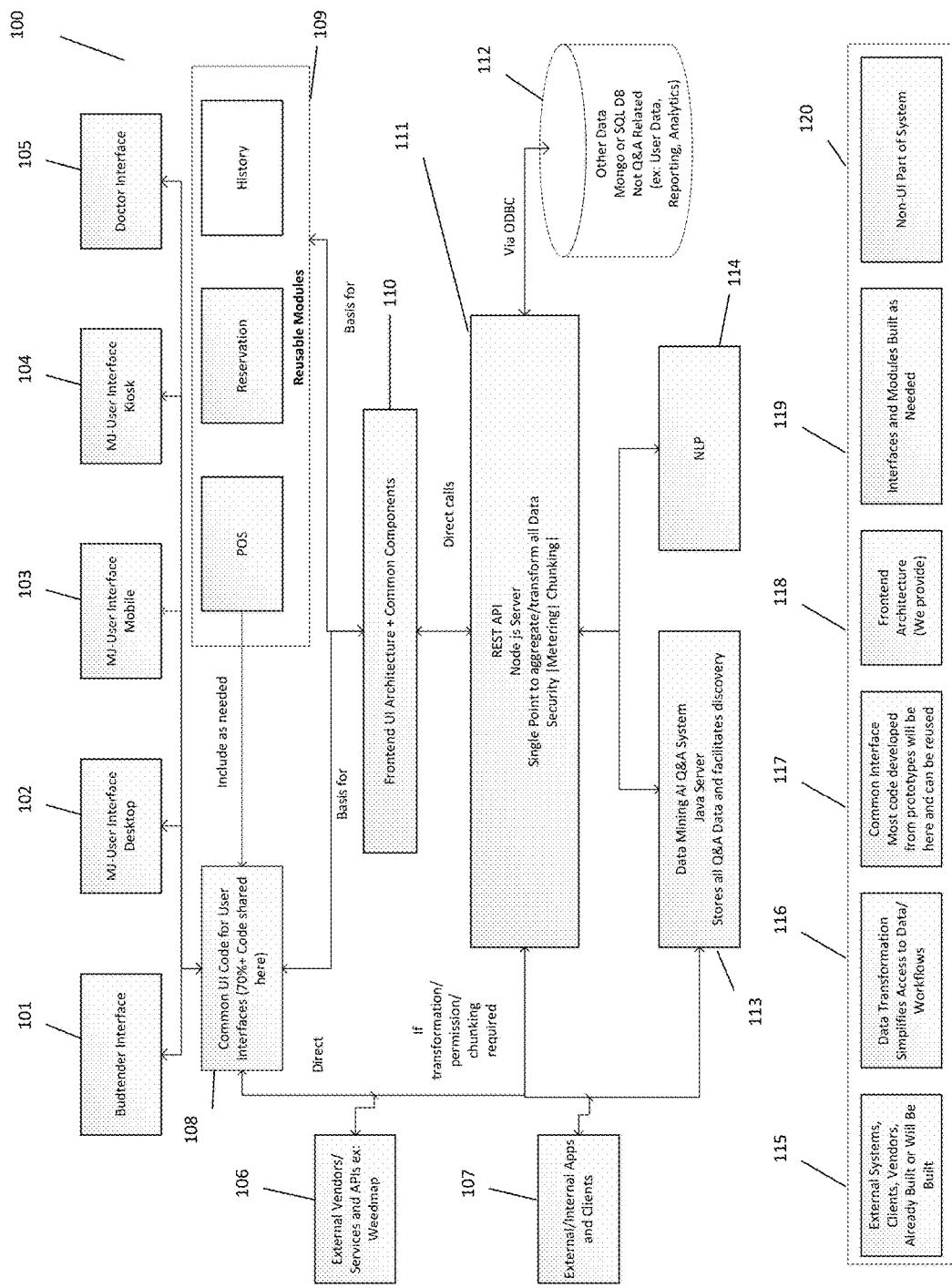
FIG. 1 is an illustration of the overall system of an embodiment comprising the computer method and apparatuses wherein the computer method operates, as well as an illustration of various components of the system by functions at the bottom.

A system 100 architecture according to embodiments is shown in FIG. 1, which shows an integrated computer method for cannabinoid treatments and selections with multiple apparatuses and components. As shown in FIG. 1, the system 100 comprises User Interfaces (UIs) 101-105, Common UI Code 108, Reusable Modules 109, External Services and Applications 106-107, Frontend UI Architecture 110, REST Application Programming Interface 111, Other Databases 112, Data Mining Artificial Intelligence 113, and Natural Language Processor 114.

User Interfaces 101-105 are computer display media displayable in desktops, mobile computers, kiosks, and other user interface media. UIs interact with the user by means of visual displays and type or touch input, and/or auditory interaction and voice recognition. UIs are where Questions and Answers (Q&A) are conducted and information collected to feed into the response loop.

User Interfaces 101-105 may be Budtender Interface 101, MJ-User Interface Desktop 102, MJ-User Interface Mobile 103, MJ-User Interface Kiosk 104, or Doctor Interface 105. Budtender Interface 101 may include Q&A concerning strain characteristics, strain availability, finished product availability and geographic location, pricing information, or other information supplied and available to growers. Budtender Interface 101 may be deployed on electronic interfaces, including laptop computers, smart phones, tablets, mobile equipment, desktop computers, or kiosks. MJ-User Interface Desktop 102, MJ-User Interface Mobile 103, and MJ-User Interface Kiosk 104 may enable interaction between patients using medical marijuana and/or medical cannabinoid products, wherein information may be collected from the user and exchanged between the user and the system. MJ-User Interfaces 102-104 may be by desktop computer, mobile computers, or by kiosks, among other possible computer interfaces. Doctor Interface 105 may include interactive sessions between the healthcare provider and the system, wherein the healthcare provider may deliver treatment information to the user and/or medical marijuana product provider, or the healthcare provider may draw information available from the system for treatment.

The UIs 101-105 may be supported by the Frontend UI Architecture 110, wherein common components of the UIs' architecture may reside. The Frontend UI Architecture 110 may serve as the basis for Common UI Code 108 and additional Reusable Modules 109. Common UI Code 108 may enable the operation of the UIs 101-105, and approximately 70% of the Frontend UI Architecture 110 code is Common UI Code 108. Additional Reusable Modules 109 may be a Point-of-Sale (POS) module, a Reservation module, a History module, or other modules produced and adapted for use within the system as needed. The POS module may enable special features in the UIs 101-105 to facilitate the sale of cannabinoid products. The Reservation module may allow the user to reserve products and/or services available to facilitate cannabinoid e-commerce. The History module may save and incorporate the user's history to enable faster services in the future. Additional modules may be available for other functions, such as a Grower module to enable seeds and nursery strains selection, or a Medical Professional's module to enable medical analyses and suggestions for treatments. Other modules may also be available to cater to the cannabinoid market stakeholders' specific needs. Reusable modules may be included as needed.

Frontend UI Architecture 110 may operate using Application Program Interface 111 (REST API). This is the application's heart, serving as the single point to aggregate and transform all data received and processed for this computer program product. The REST API 111 may also administer work flow within the computer program product, handling permission and access, as well as the program's security measures. The REST API 111 may report and meter activities within the computer program product, together with handling errors.

Feeding data to the REST API 111 may be the Data Mining Artificial Intelligence Q&A System (AI Q&A) 113 and the Natural Language Processor (NLP) 114. The AI Q&A 113 may store all data received from the UIs during Q&A and transmit it to the REST API 111 for processing. The REST API 111 may also feed command to the AI Q&A 113 based on the data received to enable the machine learning process. The AI Q&A 113 system may facilitate discovery of important information to determine the user's specific needs. The AI Q&A 113 may receive knowledge from outside sources, streamline this knowledge in a new data format conducive for storage, and analyze data using this knowledge and data received from the Q&A sessions conducted at the UIs 101-105.

Concurrently operating with the AI Q&A 113 may be the NLP 114. The NLP 114 may receive the user's input in natural language and translates it into computer-readable data, which may be fed into the REST API 111 and transmitted into the AI Q&A 113. Since the AI Q&A 113 may process data in a computer readable medium, the NLP 114 may serve as the translator between the human user and the artificial intelligence of this system. The NLP 114 may receive information in the form of natural language supplied by various users at various user interfaces, process natural language input to output data in computer readable form, and feed output data to the REST API 111.

The REST API 111 may also receive data from external sources, like the External Vendors/Services 106 and/or Internal Applications and Clients 107. External Vendors/Services 106 may be other applications and/or other Application Programming Interfaces with relevant information, e.g., WeedMaps, an application for locating medical marijuana dispensaries and marijuana strains. Other external services may also be integrated into the system for information supply in similar manners. External or Internal Applications and Clients modules 107 may collect data independent from the Q&A sessions implemented at the UIs 101-105. Data from this source may also be communicated to the AI Q&A 113 to store and determine a user's needs.

The components of the system may be External Systems 115 (built by outside parties), Data Transformation 116 (to simplify the data and allow access, conducted by the AI Q&A 113 and the REST API 111), Common Interface 117 (the basis of the user interface), Front End Architecture 118 (basis for Common Interface), Interfaces and Modules 119 (to effectuate user interface and to provide additional functionality), and Non-UI Parts 120 (to store and process data).

External Systems 115 may include systems built by clients, vendors, or other entities. External Systems 115 may interact with other components of the system to provide information, knowledge, or data input into the system. Data Transformation 116 components may process external data or input data from other components, such as Common Interfaces 117 or other Interfaces and Modules 119, into a common data format, which may be further processed by reasoners to produce outputs. Common Interface 117 may be an interface which may be used across the board by all system users. Common Interface 117 may comprise common codes, which may be displayed in all interfaces adapted to a specific kind of user. Front End Architecture 118 may be the basic code enabling the function of user interface code, including both Common Interface 117 and other Interfaces and Modules 119, as well as other components such as Point-of-Sale code, History code, and Reservation code. Front End Architecture 118 essentially may serve as the basis behind user interaction components. Interfaces and Modules 119 may serve as actual interactive components with users, wherein information may be exchanged between the system and the user. Interfaces and Modules 119 may be provided with the system, or built at a later time and employed by the system. Non-UI Part of the System 120 may be the system's non-interactive, inside components, wherein data may be processed and output may be produced.

Figure 2:
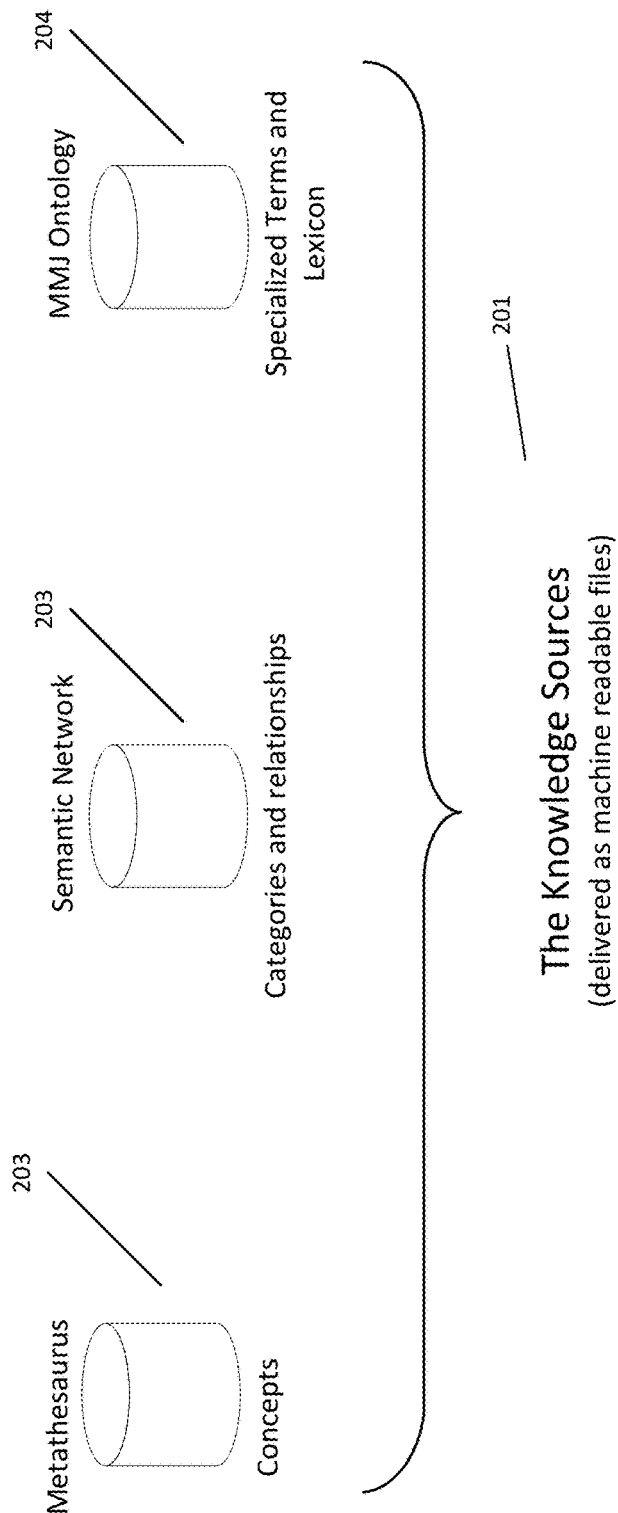
FIG. 2 is an illustration of the Knowledge Sources and its components in an embodiment. The Knowledge Sources is the primary source of knowledge upon which the system operates.

FIG. 2 depicts The Knowledge Sources 201, or the machine readable file schema, wherein medical concepts, medical marijuana knowledge, and cannabinoid knowledge may be synthesized. Three sources of knowledge for the Knowledge Sources may be the Metathesaurus 202, the Semantic Network 203, and the Medical Marijuana Ontology 204. The Medical Marijuana Ontology 204 may contain specialized terms and lexicons specific to medical marijuana applications, treatments, conditions, medical marijuana strains, cannabinoid ratios, cannabinoid products, and other cannabinoid and marijuana data. Data contained within the Medical Marijuana Ontology 204 may be provided in computer readable format.

The Knowledge Sources 201 may comprise other knowledge sources, wherein the knowledge may be incorporated to enhance the quality of analysis within the system. The Knowledge Sources may be delivered in machine-readable format from a source to the system, and the data in these files may be used in the REST API 111 for data transformation.

Figure 3:
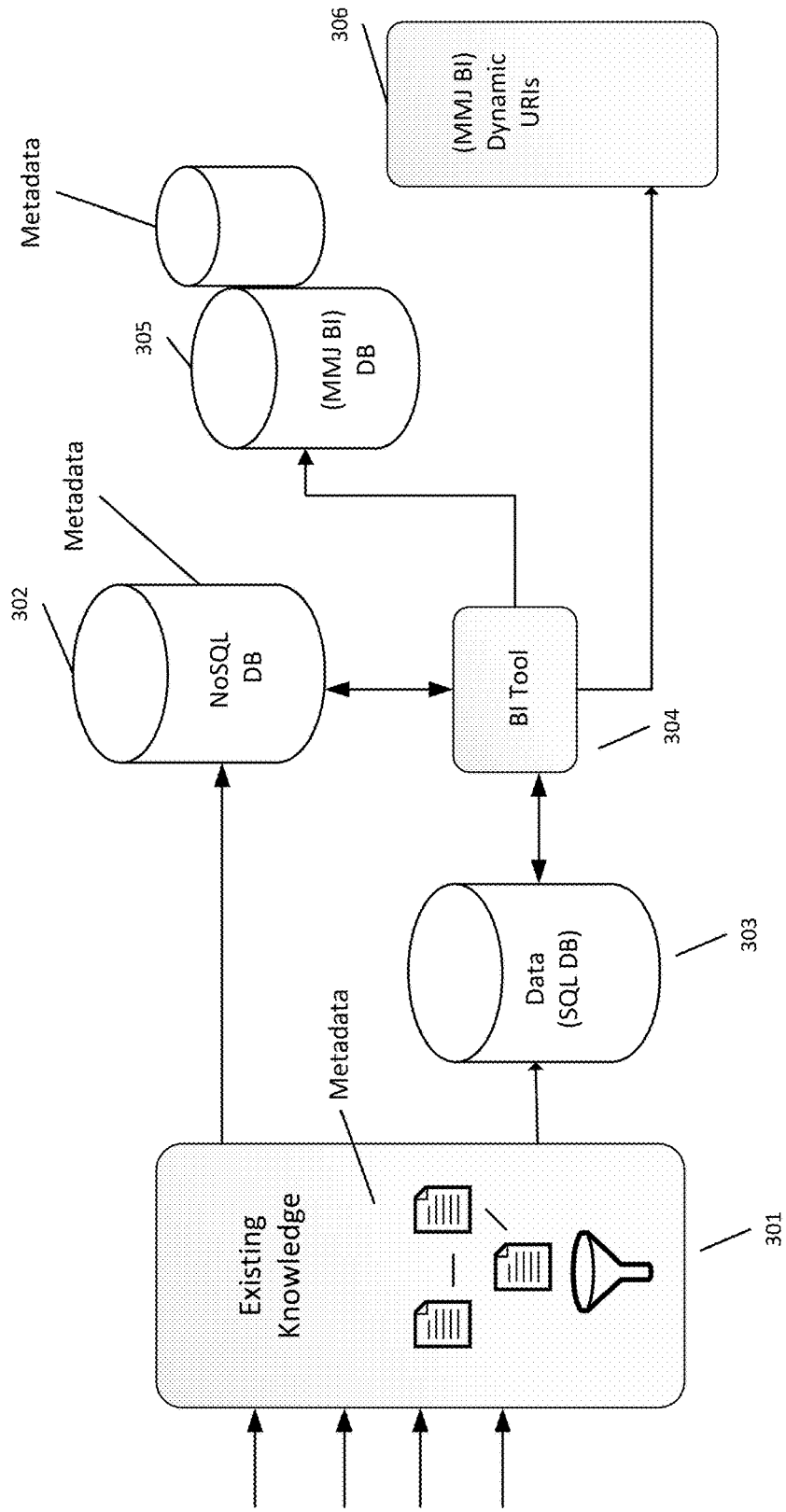
FIG. 3 is an illustration of the Dynamic Uniform Resource Identifier in an embodiment, which converts existing knowledge into a unified computer readable format to feed into the system.

FIG. 3 shows a Dynamic Unified Resource Identifier (Dynamic URI) specifically adapted to be a medical marijuana business intelligence tool. The function of the Dynamic URI may be to convert available knowledge in old data format and new data format into a uniform computer readable format. Existing Knowledge 301 may be knowledge synthesized from various sources, and may include the Knowledge Sources 201. Existing Knowledge 301, with corresponding metadata, may be transferred into SQL 303 and NoSQL 302 databases, where data chunking may be performed before the data is transferred into the Business Intelligence Tool (BI Tool) 304 for analysis. From the BI Tool 304, the data, with corresponding metadata, may be transferred to a specialized Medical Marijuana Business Intelligence Database 305 (MMJ BI DB) for analysis, relationship establishing, and business reasoning. Data from both the MMJ BI DB 305 and BI Tool 304 may be transferred into the Dynamic URI 306 for analysis and processing.

In use, a first aspect of the system may be a user interface (UI), which may present interactive question and answer sessions with the consumer to request and receive information concerning the consumer's medical symptoms and conditions. Questions displayed may be in natural language, and answers received may be in natural language, or in Boolean language by displaying Yes/No options. Questions may be adapted to users to best meet their needs. Users may be medical cannabis users, medical professionals, cannabis growers, cannabis producers, cannabis manufacturers, and cannabis salespersons.

Various UIs are depicted in FIG. 1 as 101-105. Additional collected information may include consumers' preferences on consumption routes, any allergies or counter-indications, geographical locations, and other relevant information. The UI module(s) 101-105 thereafter may transmit the collected information to a central processing unit, the REST API 111, for processing. Transmission of data from the UIs 101-105 to the REST API 111 may happen directly without processing, or indirectly, wherein data may be processed by another module prior to receipt at the REST API 111.

Other types of consumers using the UIs 101-105 may be growers, producers (budtenders), and medical professionals (doctors). Other stakeholders, including but not limited to policy makers, market researchers, and product providers, may also use appropriate interfaces to interact with the system. Different UIs 101-105 may be available for these consumers. For example, growers and producers may use the Budtender Interface 101, while medical professionals may use the Doctor Interface 105. Other types of UIs may also be used for other stakeholders' and users' specific needs in the medical marijuana and cannabinoid industry.

Once the user inputs information at the UI 101-105, the data may be transmitted into one centralized data-mining framework. The framework may include an Artificial Intelligence (AI) Reasoner, which may be capable of data mining and machine learning, connected to The Knowledge Sources 201. The AI Reasoner 113 may translate the user's input into a form to be evaluated, using new query processing and differencing techniques to mine data from existing knowledge. The Knowledge Sources 201 may compare this data with the input, the AI Reasoner may draw knowledge from the Knowledge Sources 201 and analyze the input and create an answer, which may be output at the UI 101-105. The AI Reasoner may receive data from external sources, for example The Knowledge Sources 201, to process data received from users.

The AI Reasoner may comprise multiple modules to perform the described functions. According to embodiments, the AI Reasoner may be represented by the combination of the REST API 111, the AI Q&A 113, and the NLP 114 in FIG. 1. The first module within the AI Reasoner may be a natural language processing, artificial intelligence, and net reasoning engine (NLP 114). The NLP module 114 may facilitate two way communication between the user and the apparatus, wherein the NLP module 114 may translate the user's input language into a computer readable form, then transmit the data to the Rule-Based Knowledge Base module (within the REST API 111 and AI Q&A 113) for further processing. Once the Rule-Based Knowledge Base module may output the processed data, the NLP module 114 may translate the received data into natural language and display the natural language messages to the user and the UI 101-105. The system may therefore behave as if it understands the user's language.

The second module within the AI Reasoner may be the Rule-Based Knowledge Base module. Once the NLP module 114 receives the data, the Rule-Based Knowledge Base module may process it based on a set of rules and outputs an outcome, which may be a strain and/or dose of medical marijuana, a certain ratio and/or dose of cannabinoid, a recommended administration route, product availability, product forms, or any other desired outputs. The set of rules upon which an outcome may be drawn include known medical practices for certain conditions, consumer statistics, clinical study results, molecular structures and their effects of specific cannabinoids, cannabinoid ratios of certain marijuana strains, drug interactions, known counter indications, co-morbid conditions, and other medical knowledge. This medical knowledge may be stored in and drawn from the Knowledge Sources 201.

The third module of the AI Reasoner (not shown in FIG. 1 but is within the REST API 111) may be the Metadata module. This module may interact closely with the Rule-Based Knowledge Base module, and the Rule-Based Knowledge Base module may draw information from this module for its reasoning. The Metadata module may contain knowledge and semantics encoded into the ontology schema as well as traditional metadata—data about data. Metadata may be used by the AI Reasoner both as knowledge concerning medical cannabis applications, and as inferred knowledge, such as data input date, to enhance the AI Reasoner capability. The Metadata module may receive data from The Knowledge Sources 201, encode the vocabulary and the relationships stored in The Knowledge Sources 201, and interact with the Rule-Based Knowledge Base module to provide needed data for the rule-based reasoning process.

The fourth module of the AI Reasoner may be the Q&A module and may be within the Data Mining AI Q&A System 113. This module may receive user information input during interaction with the system and store input data in its memory. Stored data may then be integrated into subsequent interactions with the same uniquely identifiable user, such that previously received data may not need to be received again, which, in turn, may reduce the user's interaction time and required steps. The Q&A module therefore may become more efficient with multiple uses by the user.

The fifth module of the AI Reasoner may be the Analytics module within Other Data 112, which may collect input from cannabis consumers from the UI 101-105 and aggregate data to analyze for trends in long-term effects, health impact, side effects, and other health aspects of using medical marijuana. This data may be shared with the data from The Knowledge Sources 201, and/or used to update data in The Knowledge Sources 201, to thereby continuously update The Knowledge Sources 201, and enable the system's machine-learning process.

The Analytics module also may collect information on consumers' choices and demands to aggregate data and analyze statistical trends to provide output on relevant market data. Manufacturers, growers, sellers, and medical professionals may use this data to study demands, trends, medical conditions, geographic distribution, market availability, and other important market information to make decision on providing products and services in medical marijuana. The collected data may also be used in medical research and policy making processes relating to medical marijuana.

The information basis for the computer program product's reasoning and analysis may be The Knowledge Sources 201. The Knowledge Sources 201 may be delivered as machine-readable files, wherein medical information and their relationships may be sourced from various sources and combined into computer-readable format. Medical conditions and biomedical vocabulary may be sourced from the Metathesaurus 202 and may be made available in many languages. Categories of medical and biomedical vocabulary and their relationships may be sourced from the Semantic Network 203. The Knowledge Sources 201 may also incorporate information from a third database called the MMJ Ontology 204. The MMJ Ontology 204 may comprise information on various aspects of medical marijuana, including: information of specific strains of medical marijuana and their cannabinoid ratios; variations among the strains; products made from the specific strains; methods for administration; recommended medical conditions for each medical marijuana strains and/or cannabinoid ratios and/or doses; relationships between medical conditions and marijuana strains or cannabinoids; availability of products in each geographic area; and availability of medical services relating to medical marijuana and/or cannabinoid treatments, among other information. Other sources may also be used to enhance information synthesized in the Knowledge Sources 201.

The Metathesaurus 202 may include, among other sources, The Alcohol and Other Drug Thesaurus: Terminology in Abuse and Addiction (AOD) and The Beth Israel On-line Medical Record (OMR) Clinical Problem Vocabulary. The inclusion of these sources may enhance the information database, increase the ability of The Knowledge Sources 201, and facilitate identification of relationship between specialized terms and lexicons in the MMJ Ontology 204, terms and relationships in The Metathesaurus 202 and The Semantic Network 203.

The Knowledge Sources 201 first may encode the combined information from these three sources into an ontology schema, then use domain-independent linguistic and lexical resources to process and understand input information from the various UIs 101-105. User interaction at the UIs 101-105 may be conducted in different natural languages, and the linguistic and lexical resources may enable input information processing to appropriate output responses in the language used for input.

The Knowledge Sources 201 may alternatively or additionally supply information and data to the Dynamic Unified Resource Identifier 306 for further processing, with the goal of providing processed information based on both existing scientific knowledge concerning medical marijuana and cannabinoid treatment and business information as embedded in the Dynamic URI 306. Data output from the Dynamic URI 306 may be supplied to the system in addition to, or as an alternative to the Knowledge Sources 201.

The Dynamic Unified Resource Identifier 306 may serve to convert existing information and knowledge and deliver it in a uniform computer readable format. The Dynamic Unified Resource Identifier 306 may act as the "translator" as well as the "synthesizer" of information from the Knowledge Sources 201 and feed data to the system. Data may be drawn from the Knowledge Sources 201 and/or other sources and synthesized as Existing Knowledge 301 within the Dynamic URI 306 with corresponding metadata. Data from Existing Knowledge 301 may be transferred to at least one database, which may be SQL 303 or NoSQL 302 databases for chunking and establishing of dynamic schema and relationship between data, if any. The use of both SQL and NoSQL databases may enhance available options for data storage and establishment of data relationship. After chunking and establishment of relationship, data may be transferred to Business Intelligent Tool 304 for analysis, using received data and existing commands built-on in the BI Tool 304. From the BI Tool 304, data may be transferred into the Medical Marijuana Business Intelligence Database (MMJ BI DB) 306, wherein specified knowledge and information on medical marijuana business may be stored. Using data from the BI Tool 304, the MMJ BI DB 306 may further process available data in light of the knowledge in the MMJ BI DB 306, specifically for analysis, relationship establishing, and business reasoning. Finally, data from BI Tool 304 and MMJ BI DB 306 may be transferred to the Dynamic URI 306 for further analysis and processing, before being supplied to the system.

This computer method may be hosted and performed by a plurality of computer hardware. The UIs 101-105 may be hosted on various computing hardware, including but not limited to desktop computers, laptop computers, smart phones, tablets, kiosk, and/or other computing hardware. External Applications and Services 106-107 may be hosted on different computing medium or on the same computing medium with the UIs 101-105. Frontend UI Architecture and its modules 108-109, REST API 111, AI Q&A 113, NLP 114, and other databases 112 may be hosted on the same computing hardware with the UIs 101-105, on a different computing hardware, or on a remote computing medium. Preferably, modules that are not UIs may be hosted on remote computing medium(s), including cloud computing, to enable faster processing.

In operation, the system 100 may operate to display questions in natural language and receiving answers from a user at a user interface 101-105. Questions displayed may be adapted to user types to tailor to the user's specific need. Answers received may be in natural language, which may be converted to computer readable data format by a processor such as the NLP 114. Answers may also be in Boolean format. Computer readable data may be processed by artificial intelligence reasoning using data from at least one knowledge source, which may be the Knowledge Sources 201 to produce at least one output. Other knowledge sources may also be used for artificial intelligence reasoning. Additionally, certain users, such as medical professionals, may upload data, including aggregate data to the system, which is stored within the Knowledge Sources 201 and may be used during artificial intelligence reasoning. The at least one output may be converted into natural language by a processor, such as the NLP 114, which may be displayed at a User Interface 101-105.

It should be noted that the above-described functionality may be implemented using appropriate hardware and/or software component. In one embodiment, the functionality is implemented on an article of manufacture comprising a computer-readable storage medium and computer-readable data stored therein. Examples of the article may include, but are not limited to, an electronic storage medium having electronic data, a magnetic storage medium having magnetic data, and an optical storage medium having optical data.

This system may provide an overall interactive user-based system to address the consumer's needs and demands for medical marijuana, while at the same time gathering data from users to improve the system's answer quality. The system may also collect information and output useful information for manufacturers, medical professionals, growers, and merchants to make decisions in their businesses. This system may also be useful in policy making, in that various trends and needs may be tracked and new policies may be implemented to ensure the smooth operation of the medical marijuana market as a whole.

Medical marijuana research has long been available in the form of various published documents discussing various studies. This system may convert this medical marijuana knowledge base into a computer readable medium, integrate other available knowledge bases, such as the Metathesaurus and the Semantic Network within the USML®, and analyze the relationships between medical vocabularies and medical marijuana knowledge to output appropriate responses, while at the same time collecting information for actual consumers of medical marijuana and using this information to continually update the system's embedded knowledge base. While the system may be specifically useful for medical marijuana consumers, it may also be used for other stakeholders in the medical marijuana industry and policy and lawmakers.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. A method to provide medical cannabis diagnosis, treatment, research, market analysis, production decision, and policy making, comprising:
   displaying questions in natural language and receiving answers from a user at a user interface, wherein the questions are adapted to the user and the user is selected from a group consisting of a medical cannabis user, a medical professional, a cannabis grower, a cannabis producer, a cannabis manufacturer, and a cannabis salesperson;
   converting the answers to computer readable data using a natural language processor;
   collecting metadata from the computer readable data;
   processing the computer readable data based on a set of rules, the set of rules is medical practices for certain conditions, consumer statistics, clinical study results, effects of specific cannabinoids, cannabinoid ratios of certain marijuana strains, drug interactions, counter indications, or co-morbid conditions and based on metadata collected to produce received computer readable data;

receiving computer-readable data from at least one outside source, wherein the at least one outside source provides information on medical conditions, biomedical vocabulary, specific strains of medical marijuana and their cannabinoid ratios, variations among the strains, products made from the specific strains; methods for administration, recommended medical conditions for each medical marijuana strains, cannabinoid ratios, relationships between medical conditions and marijuana strains or cannabinoids, availability of products in each geographic area, or availability of medical services relating to medical marijuana or cannabinoid treatments;

processing the received computer readable data using computer-readable data from outside sources to produce at least one output;

converting the at least one output into natural language using a natural language processor; and displaying the at least one output in natural language at the user interface, wherein the user interface is a computing article and the computing article is a desktop computer, a laptop computer, a smart phone, a tablet, or a kiosk computer, and wherein the natural language processor is configured to convert natural language to computer readable data and convert computer readable data into natural language.

2. The method of claim 1, wherein the at least one outside source is the Metathesaurus, the Semantic Network, and the Medical Marijuana Ontology.

3. The computer method of claim 2, wherein the Medical Marijuana Ontology comprises medical cannabis data provided in computer readable files.

4. The method of claim 1, wherein the questions displayed at the user interface comprises questions on uniquely identifiable information for each user, symptoms, medical conditions, preference on consumption routes, allergies, counter-indications, geographical locations.

5. The method of claim 1, further comprising the steps of:
identifying the user and designate the user with uniquely identifiable information;
storing data received from the uniquely identified user;
tailoring questions displayed to the uniquely identifiable user to avoid receiving already stored information.

6. The method of claim 1, further comprising the step of aggregating the received computer readable data from the user to analyze for trends in long-term effects, health impact, side effects of using medical cannabis, consumers' choices and storing the aggregated data.

7. The method of claim 6, further comprising the step of sharing the aggregated data with outside information sources.

8. A computer-based system for medical cannabis diagnosis, treatment, market analysis, production decision, and policy making, the system comprising:
an article of manufacture comprising computer-readable storage media having processor executable instructions stored thereon;
at least one user interface module provided on a computer article, the computing article is a desktop computer, a laptop computer, a smart phone, a tablet, or a kiosk computer;
a first software to serve as the basis for the user interface module that, when executed by one or more processors, displays questions to users on the at least one user interface, the questions adapted for a group consisting of medical cannabis users, medical professionals, cannabis growers, cannabis producers, cannabis manufacturers, and cannabis salespersons;
at least one natural language processor to process user input into computer readable data and process computer readable data produced from software in the computer-based system to natural language, wherein the natural language processor processes or receives information from the user interface module and from the software;
a second software to serve as the single point data analysis that, when executed by one or more processors, directs the one or more processors to:
receive computer readable data from the at least one natural language processor;
process data received based on a set of rules, the set of rules is medical practices for certain conditions, consumer statistics, clinical study results, effects of specific cannabinoids, cannabinoid ratios of certain marijuana strains, drug interactions, counter indications, or co-morbid conditions;
collect metadata from the computer readable data and use this metadata to process data received;
aggregate received data to analyze for trends in long-term effects, health impact, side effects of using medical cannabis, or consumers' choices;
share aggregated data with outside sources;
provide information to cannabis medical cannabis users, medical professionals, cannabis growers, cannabis producers, cannabis manufacturers, or cannabis salespersons; and
a third software to serve as the knowledge source that, when executed by one or more processors, directs the one or more processors to:
receive computer-readable data from the second software;
receive computer-readable data from outside sources, wherein the outside sources provide information on medical conditions, biomedical vocabulary, specific strains of medical marijuana and their cannabinoid ratios; variations among the strains; products made from the specific strains; methods for administration; recommended medical conditions for each medical marijuana strains, cannabinoid ratios; relationships between medical conditions and marijuana strains or cannabinoids; availability of products in each geographic area; and availability of medical services relating to medical marijuana or cannabinoid treatments; and
process data received from the second software and the outside sources; and
provide processed data to the natural language processor.

9. The system of claim 8, wherein the outside sources comprise the Metathesaurus, the Semantic Network, and the Medical Marijuana Ontology.

10. The system of claim 8, wherein the outside source comprises a Dynamic Uniform Resource Identifier.

11. The system of claim 10, wherein the Dynamic Uniform Resource Identifier comprises:
at least one existing knowledge database;

at least one of an SQL server or a NoSQL server to receive and store data from the at least one existing knowledge database;
at least one business intelligence tool, the business intelligence tool comprises stored data and computer-executable commands;
at least one medical marijuana business intelligence database wherein knowledge and information on medical marijuana business is stored; and
a uniform resource identifier;
wherein the SQL and NoSQL servers supply data to the business intelligence tool;
wherein the business intelligence tool supplies data to the medical marijuana business intelligence knowledge database; and
wherein the medical marijuana business intelligence knowledge database and the business intelligence tool analyze and supply data to the uniform resource identifier.

12. The system of claim 8, further comprising at least one reusable module.

13. The system of claim 12, wherein the at least one reusable module is selected from the group consisting of Point-of-Sale module, Reservation module, and History module.

14. The system of claim 13, further comprising at least one additional database to supply data to the third software.

15. The system of claim 14, further comprising an external service, wherein the external service is an outside software suppling additional information for the computer-based system, the external service is not provided by the computer-based system.

16. The computer-based system of claim 8, wherein the second software further comprises:
when executed by one or more processors, directs the one or more processors to:
identify the user and designate the user with uniquely identifiable information;
store data received from the uniquely identified user;
tailor questions displayed to the uniquely identified user to avoid receiving already stored information.

* * * * *